United States Patent [19]

Chan et al.

[11] Patent Number: 5,240,568
[45] Date of Patent: Aug. 31, 1993

[54] REMOVAL OF ACETOPHENONE FROM PHENOL PURIFICATION RESIDUES

[75] Inventors: Chong H. Chan, Richmond; Lamberto Crescentini, Chester; Everett H. Hinton, Jr., Chester; Laszlo J. Balint, deceased, late of Chester, all of Va., by Gisella F. Balint, executrix.

[73] Assignee: Allied-Signal Inc., Morris Township, Morris County, N.J.

[21] Appl. No.: 756,269

[22] Filed: Aug. 29, 1991

[51] Int. Cl.$^5$ .......................... B01D 3/14; C07C 37/74
[52] U.S. Cl. ......................... 203/84; 203/65; 203/78; 203/DIG. 19; 568/324; 568/335; 568/754
[58] Field of Search ............ 203/78, 84, 65, DIG. 19, 203/99; 568/324, 335, 754, 749

[56] References Cited

U.S. PATENT DOCUMENTS

| | | | |
|---|---|---|---|
| 2,727,074 | 12/1955 | Bewley | 568/324 |
| 2,750,424 | 6/1956 | Armstrong et al. | 568/324 |
| 2,757,209 | 7/1956 | Joris | 568/754 |
| 2,906,789 | 9/1959 | McNaughton | 568/324 |
| 3,441,618 | 4/1969 | Flickinger | 568/754 |
| 4,415,409 | 11/1983 | Zudkevitch et al. | 568/749 |
| 4,544,776 | 10/1985 | Osterburg et al. | 203/DIG. 19 |
| 4,559,110 | 12/1985 | Swearingen et al. | 203/37 |
| 5,046,507 | 11/1991 | O'Donnell | 203/DIG. 19 |

OTHER PUBLICATIONS

Chemical Abstracts, Vol. 83 No. 21 Nov. 24, 1975 Columbus, Ohio, U.S.; Abstract No. 178548m.

Primary Examiner—Wilbur Bascomb, Jr.
Attorney, Agent, or Firm—William H. Thrower

[57] ABSTRACT

A process for separating phenol obtained by the decomposition of cumene hydroperoxide from high boiling impurities, includes the following steps:

a) feeding phenol rectification bottoms comprising phenol, acetophenone, cumylphenol, alpha-methylstyrene dimers and high boiler residues to a first phenol freeing distillation column A;

b) feeding concentrated bottoms with substantially reduced phenol content from column A to a second residue concentration distillation column B;

c) withdrawing a stream rich in compounds boiling between phenol and residue, particularly cumylphenol, from said column B from a point below the feed and returning at least a portion of said stream to said column A at a point above the feed;

d) recovering overheads from column A comprising at least 95 weight percent phenol; and e) recovering acetophenone-rich overheads from column B comprising at least 70 weight percent acetophenone.

5 Claims, 1 Drawing Sheet

REMOVAL OF ACETOPHENONE FROM PHENOL PURIFICATION RESIDUES

BACKGROUND OF THE INVENTION

1. Field of the Invention

The invention relates to a process for rectifying product phenol obtained by the acid-catalyzed decomposition of cumene hydroperoxide.

2. Description of Related Art

Phenol produced by the acid-catalyzed decomposition of cumene hydroperoxide is conventionally purified via a series of distillations in which progressively heavier components of the decomposition mixture are separated as overheads.

The decomposition product is neutralized, typically in an alkaline ion exchanger, before being separated into products phenol and acetone, by-products, and unreacted cumene for recycle.

The decomposition mass is separated sequentially into acetone, cumene, alpha-methylstyrene (AMS), phenol and high boiling residues. Phenol, acetone and AMS are further purified into end products. Recovered cumene is caustic washed to rid it of acidity before recycle to oxidation. The separation of the crude decomposition mass is carried out in a series of fractionating distillation columns in commercial operation.

Phenol purification is carried out in vacuum distillation columns usually equipped with from 30 to 40 vapor-liquid counter current contact trays or equivalent height of mass transfer packed beds.

Considerable amounts of phenol remain with higher boilers in the bottoms of the final distillation column in which product phenol is rectified, and obtained as an overhead stream.

To insure adequate quality for the phenol in the overheads, typically greater than 15% phenol is left in the bottoms of such phenol rectification column, along with heavy impurities such as acetophenone, cumylphenol, alpha-methylstyrene dimers (AMS dimers) and other high boilers (residue). Although an attempt is made in a subsequent residue column to recover more phenol, albeit of a lesser quality, in order to reduce the amount lost with high boilers in those bottoms, phenol still represents at least 5% of the total residual high boilers. These are usually burned to recover only heat values.

Furthermore, the overheads of such subsequent residue column, predominantly phenol, contain too much acetophenone to be acceptable as product, thus are recycled upstream in the process, for rework.

U.S. Pat. No. 4,415,409 to Zudkevitch et al. discloses a process for extractive distillation of phenol and acetophenone using cumylphenol as an extractive solvent. However, this patent does not teach or suggest the combination of distillation steps and the added advantages of the process claimed herein.

SUMMARY OF THE INVENTION

In a process for separating phenol obtained by the decomposition of cumene hydroperoxide from high boiling impurities, the improvement comprising:

a) feeding phenol rectification bottoms comprising phenol, acetophenone, cumylphenol, alpha-methylstyrene dimers and high boiler residues to a first phenol freeing distillation column A;

b) feeding concentrated bottoms with substantially reduced phenol content from column A to a second residue concentration distillation column B;

c) withdrawing a stream rich in compounds boiling between phenol and residue, particularly cumylphenol, from said column B from a point below the feed and returning at least a portion of said stream to said column A at a point above the feed;

d) recovering overheads from column A comprising at least 95 weight percent phenol; and e) recovering acetophenone-rich overheads from column B comprising at least 70 weight percent acetophenone.

DESCRIPTION OF THE PREFERRED EMBODIMENT

We have now developed an improvement by which additional phenol with good purity can be recovered from conventional phenol rectification bottoms; acetophenone can be isolated in a relatively concentrated form which has commercial value; a cumylphenol-rich stream can be separated for recovery of cumylphenol values; and the amount of phenol lost with the residue can be reduced substantially.

Figure 2:
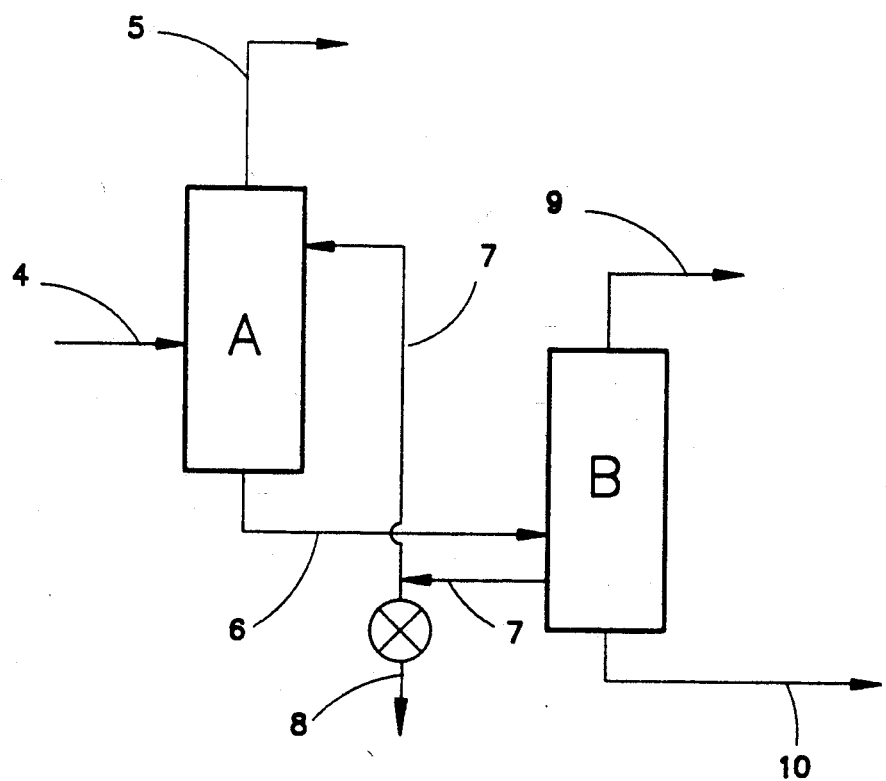
FIG. 2 shows a schematic diagram of the process of this invention practiced in example 2.

This improved process is illustrated in FIG. 2. Bottoms from a phenol rectification column comprising recoverable amounts of phenol, acetophenone, and cumylphenol together with AMS dimers and high boiling residue are fed through line 4 to an intermediate point of a phenol freeing continuous distillation column A. Column A is preferably 15 to 30 trays and is operated at a reflux ration of 1.5:1 to 2.5:1 and at reduced pressure, preferably less than 50 mmHg measured at the top to minimize thermal decomposition. As known in the art, packing can be substituted for the trays referred to herein. The column A is operated under conditions to produce concentrated column bottoms with substantially reduced phenol content.

The concentrated bottoms from column A, with substantially reduced phenol content, are fed via line 6 to an intermediate point of a second residue concentration continuous distillation column B. Column B is preferably 10 to 20 trays and is operated at a reflux ratio and reduced pressure similar to column A.

A stream enriched in compounds boiling between phenol and residue is withdrawn from column B via line 7, from below feed line 6, and is returned to column A at a point above feed line 4. As a result of this return the overheads from column A, removed via line 5, are a much purer phenol distillate. In particular, acetophenone is present at a much lower concentration. The overheads from column A comprise at least 95 weight percent phenol, preferably at least 99 weight percent phenol. A portion of the stream removed via line 7 can be removed via line 8 and may be further refined to recover cumylphenol. Alternatively, that portion removed via line 8 may be burned to recover fuel value. The overheads removed from column B via line 9 consist predominately of acetophenone, for example at least 70 weight percent and have commercial value. The bottoms from column B removed via line 10 can be burned to recover fuel valve. As a result of this process there is a substantial reduction in the amount of phenol lost with the residue.

EXAMPLE 1

(Comparative)

Figure 1:
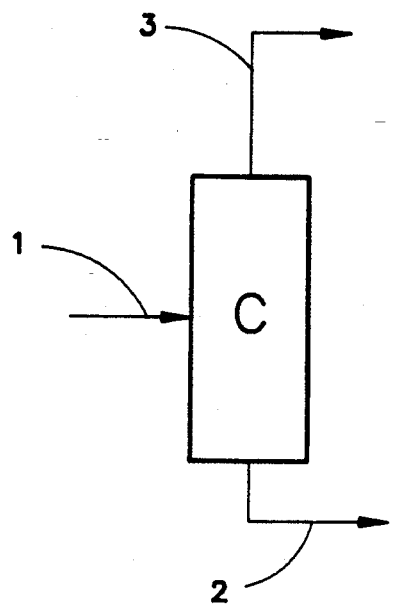
FIG. 1 shows a schematic diagram of the prior art representing comparative example 1.

Bottoms from a phenol rectification column having the composition 1' given in Table I are fed via line 1 to the 11th tray of a 20-tray continuous distillation column C operated at 35 mmHg pressure overhead and a reflux ratio of 3. (FIG. 1). Overhead and bottoms streams are withdrawn through lines 3 and 2 having composition 8' and 9', respectively. As can be seen from Table I, phenol in the overheads is contaminated by about 18% acetophenone and a substantial amount of phenol is lost with the bottoms.

EXAMPLE 2

A stream having composition 1' (Table II), the same as (used as) feed in comparative example 1, is fed via line 4 to the 12th tray of a 20-tray continuous distillation column A operated at 35 mmHg pressure overhead and a reflux ratio of 2 (FIG. 2). The bottoms from this column, removed via line 6, have composition 4' and are fed via line 6 to the 10th tray of a 15-tray column B. A stream with composition 2', enriched in compounds boiling between phenol and residue is withdrawn via line 7 from the 5th tray of column B and returned to the 15th tray of column A via line 7. As a result of this addition, the overheads from column A, removed via line 5, are much purer phenol distillate (composition 3', Table II). In particular, acetophenone is present at much lower concentration (0.5% vs. 18.5%). A portion of the stream with composition 2' is withdrawn via line 8 (composition 7' Table II) and may be further refined if desired to recover cumylphenol. Alternatively, that portion removed via line 8 may be burned to recover fuel value. The overheads removed from column B via line 9 have composition 5' and consist predominantly of acetophenone. The bottoms from column B, removed via line 10 have composition 6' and can be burned to recover fuel value. As can be seen, much less phenol is lost with the residue than in example 1 (0.2 vs. 3.9 parts).

The examples are given for illustrative purposes and the process of the invention can be carried out at conditions similar but not identical to those specified in example 2. For instance, the number of trays in the column may vary, feed and withdrawal points may be changed, provided line 7 always is added at a higher tray and than line 4 to column A and line 7 always exits column B lower than line 6 enters column B.

Amounts of material withdrawn from column B via line 7 may vary between 100 and 200% of the amount of feed to column A. Total cumylphenol added to column A via line 7 should be no less than 4 times the total amount of acetophenone added to column A.

TABLE I

| | MASS BALANCE CONVENTIONAL PROCESS | | | | | |
|---|---|---|---|---|---|---|
| COM- | 1' | | 8' | | 9' | |
| POSITIONS | PARTS | % | PARTS | % | PARTS | % |
| PHENOL | 21.1 | 21.1 | 17.2 | 81.5 | 3.9 | 4.9 |
| ACETO-PHENONE | 16.1 | 16.1 | 3.9 | 18.5 | 12.2 | 15.5 |
| CUMYL-PHENOL | 27.8 | 27.8 | TR | | 27.8 | 35.2 |
| AMS DIMERS | 17.1 | 17.1 | TR | | 17.1 | 21.7 |
| RESIDUE | 17.9 | 17.9 | TR | | 17.9 | 22.7 |
| TOTAL | 100.0 | 100.0 | 21.1 | 100.0 | 78.9 | 100.0 |

Note:
Figures are parts by weight
TR = Trace
Only major identified impurities are shown.

TABLE II

| | MASS BALANCE NEW PROCESS | | | | | | | | | | | | | |
|---|---|---|---|---|---|---|---|---|---|---|---|---|---|---|
| COM- | 1' | | 2' | | 3' | | 4' | | 5' | | 6' | | 7' | |
| POSITIONS | PARTS | % | PARTS | % | PARTS | % | PARTS | % | PARTS | % | PARTS | % | PARTS | % |
| PHENOL | 21.1 | 21.1 | TR | | 19.1 | 99.5 | 2.0 | 0.9 | 1.9 | 10.4 | 0.1 | 0.3 | TR | |
| ACETO-PHENONE | 16.1 | 16.1 | 6.5 | 4.4 | 0.1 | 0.5 | 22.5 | 9.8 | 14.3 | 78.6 | 0.5 | 1.4 | 1.2 | 4.4 |
| CUMYL-PHENOL | 27.8 | 27.8 | 97.3 | 65.7 | TR | | 125.1 | 54.6 | 0.9 | 5.0 | 8.9 | 25.3 | 18.0 | 65.7 |
| AMS DIMERS | 17.1 | 17.1 | 34.1 | 23.0 | TR | | 51.2 | 22.4 | 1.1 | 6.0 | 9.7 | 27.6 | 6.3 | 23.0 |
| RESIDUE | 17.9 | 17.9 | 10.3 | 6.9 | TR | | 28.2 | 12.3 | TR | | 16.0 | 45.4 | 1.9 | 6.9 |
| TOTAL | 100.0 | 100.0 | 148.2 | 100.0 | 19.2 | 100.0 | 229.0 | 100.0 | 18.2 | 100.0 | 35.2 | 100.0 | 27.4 | 100.0 |

Figures are parts by weight
TR = Trace
Only major impurities are considered

What is claimed is:

1. In a process for separating phenol obtained by the decomposition of cumene hydroperoxide from high boiling impurities comprising distillation in a phenol rectification column to obtain product phenol overhead and phenol rectification bottoms containing phenol, the improvement comprising:
    a) feeding said phenol rectification bottoms comprising phenol, acetophenone, cumylphenol, alpha-methylstyrene dimers and high boiler residue to a first phenol freeing distillation column A;
    b) feeding concentrated bottoms with substantially reduced phenol content from column A to a second residue concentration distillation column B;
    c) withdrawing a side stream rich in compounds boiling between phenol and high boiler residue from said column B from a point below the feed and returning at least a portion of said side stream to said column A at a point above the feed of column A;
    d) recovering overheads from column A comprising at least 95 weight percent phenol; and
    e) recovering acetophenone-rich overheads from column B comprising at least 70 weight percent acetophenone.

2. The process of claim 1 wherein a second portion of said side stream rich in compounds boiling between phenol and high boiler residue is removed.

3. The process of claim 2 wherein said side stream comprises at least 60 weight percent cumylphenol.

4. The process of claim 2 wherein the total weight of cumylphenol added to column A is at least 4 times the total weight of acetophenone added to column A.

5. The process of claim 4 wherein the total weight of cumylphenol added to column A is at least 5.5 times the total weight of acetophenone added to column A.

* * * * *